(12) United States Patent
Morsi

(10) Patent No.: US 8,048,091 B2
(45) Date of Patent: Nov. 1, 2011

(54) SUTURING DEVICE FOR ANASTOMISIS OF LUMENS

(76) Inventor: Hesham Morsi, Houston, TX (US)

( * ) Notice: Subject to any disclaimer, the term of this patent is extended or adjusted under 35 U.S.C. 154(b) by 341 days.

(21) Appl. No.: 12/417,994

(22) Filed: Apr. 3, 2009

(65) Prior Publication Data

US 2009/0254101 A1 Oct. 8, 2009

Related U.S. Application Data

(60) Provisional application No. 61/043,320, filed on Apr. 8, 2008.

(51) Int. Cl.
A61B 17/10 (2006.01)
(52) U.S. Cl. ....................................................... 606/139
(58) Field of Classification Search .......... 606/139–158, 606/205–211; 227/175.1
See application file for complete search history.

(56) References Cited

U.S. PATENT DOCUMENTS 3,254,651 A * 6/1966 Collito ........................... 606/153
2002/0058955 A1* 5/2002 Blatter et al. .................. 606/153
* cited by examiner Primary Examiner — Melanie Tyson
Assistant Examiner — Son Dang
(74) Attorney, Agent, or Firm — David McEwing

(57) ABSTRACT

A surgical device that includes an outer hollow body and an inner hollow body. The inner hollow body is slidably disposed within said outer hollow body and the inner hollow body includes at least two hollow arms located at the distal end of the inner hollow body. An inflatable member is rotatably attached to each hollow arm of the inner hollow body. At least a pair of suture rings are rotatably coupled to the outer hollow body wherein the suture rings are in parallel to each other and are coupled to each other by a plurality of suture clips.

8 Claims, 10 Drawing Sheets

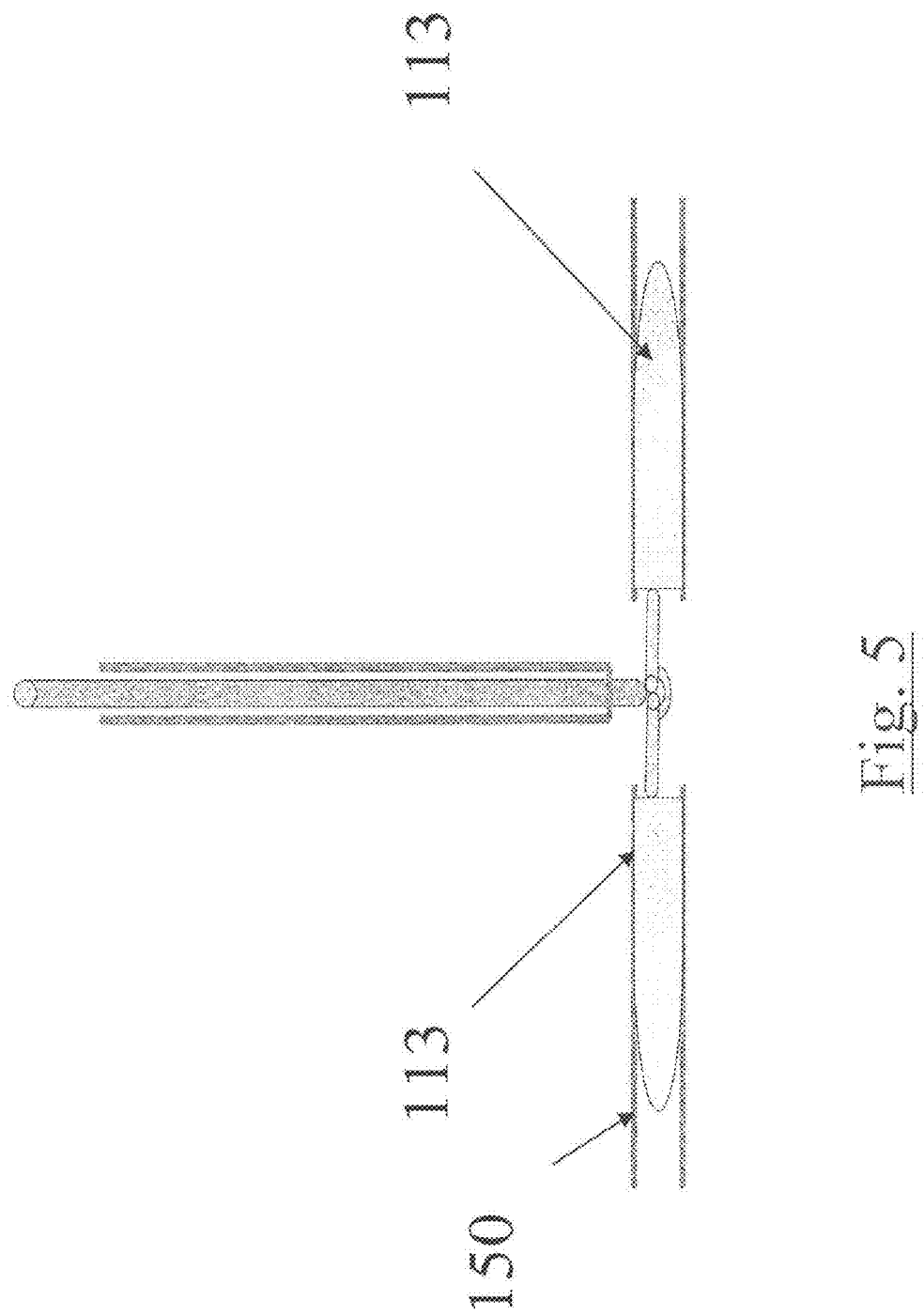

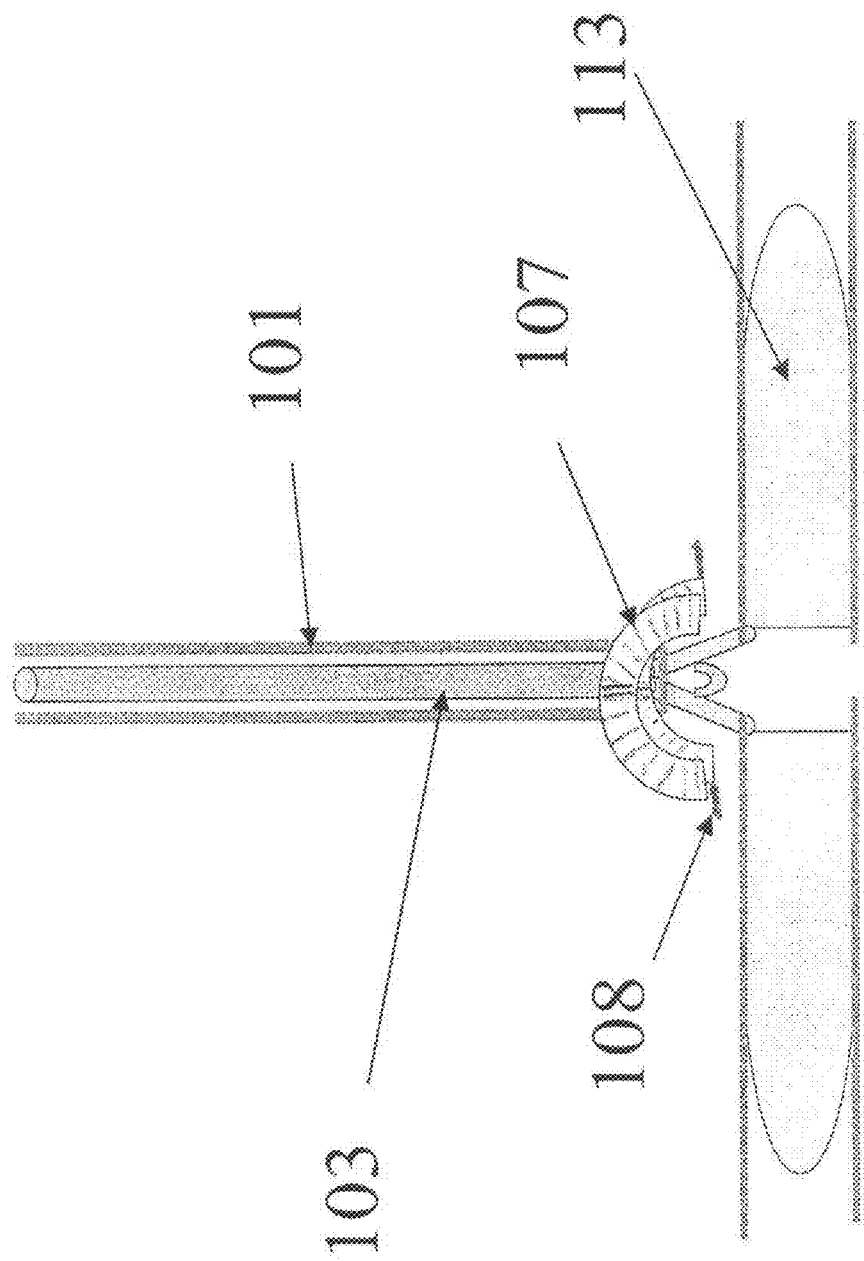

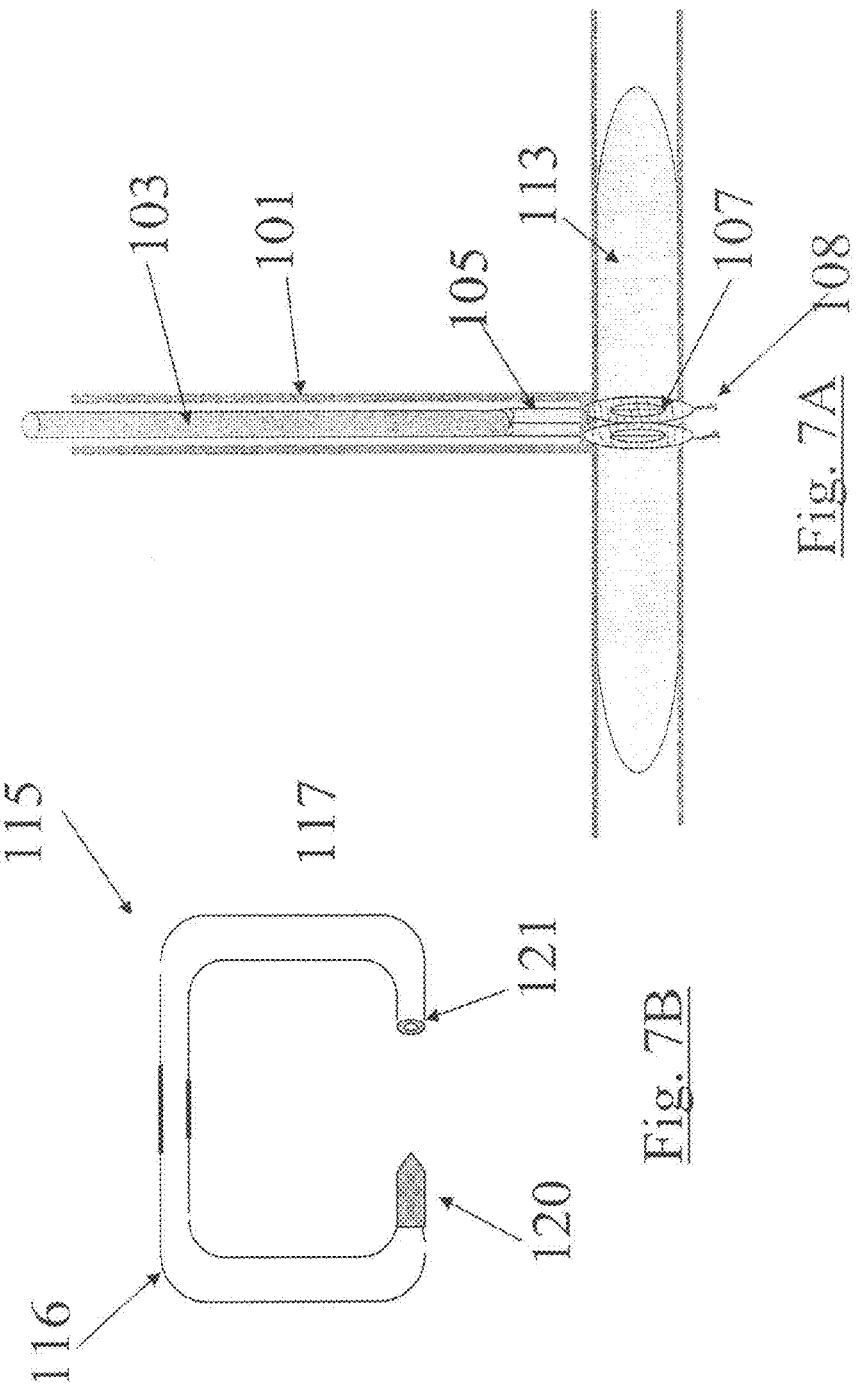

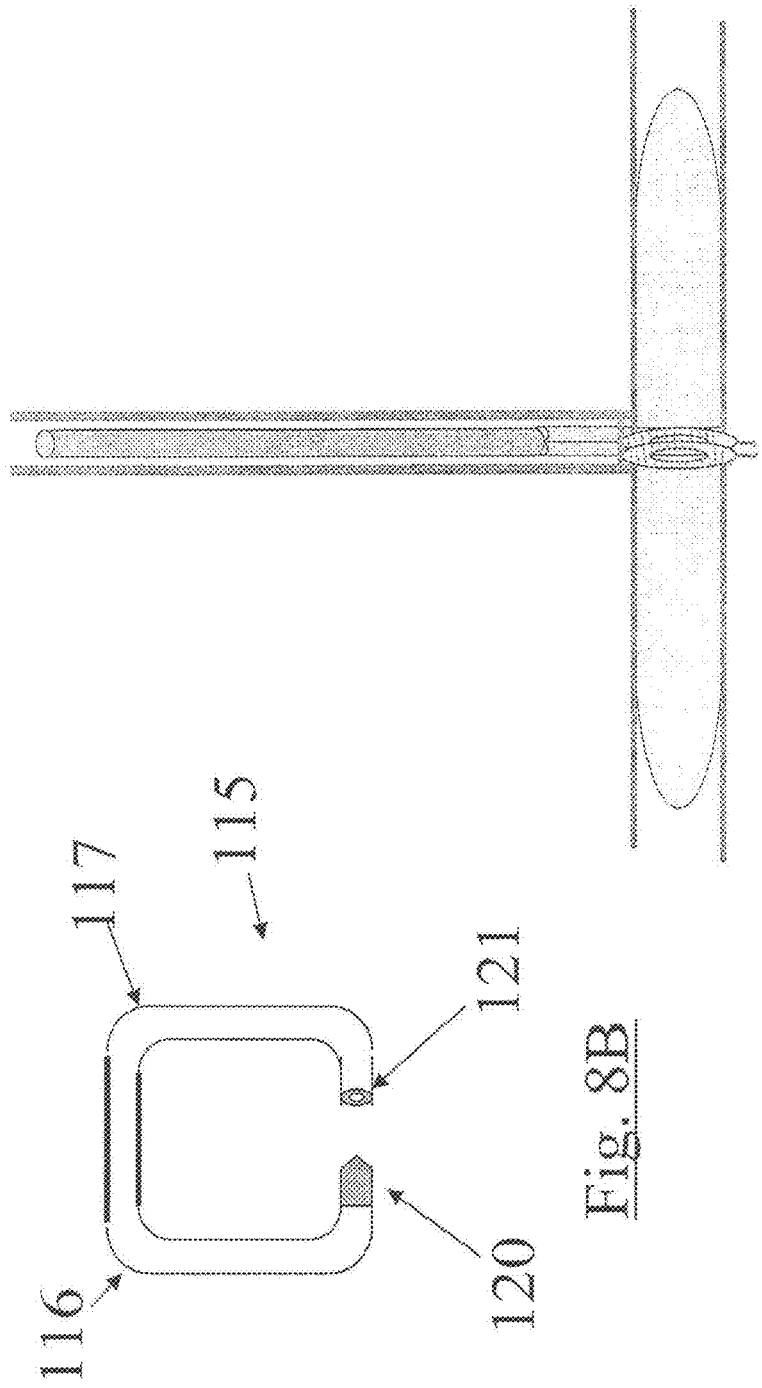

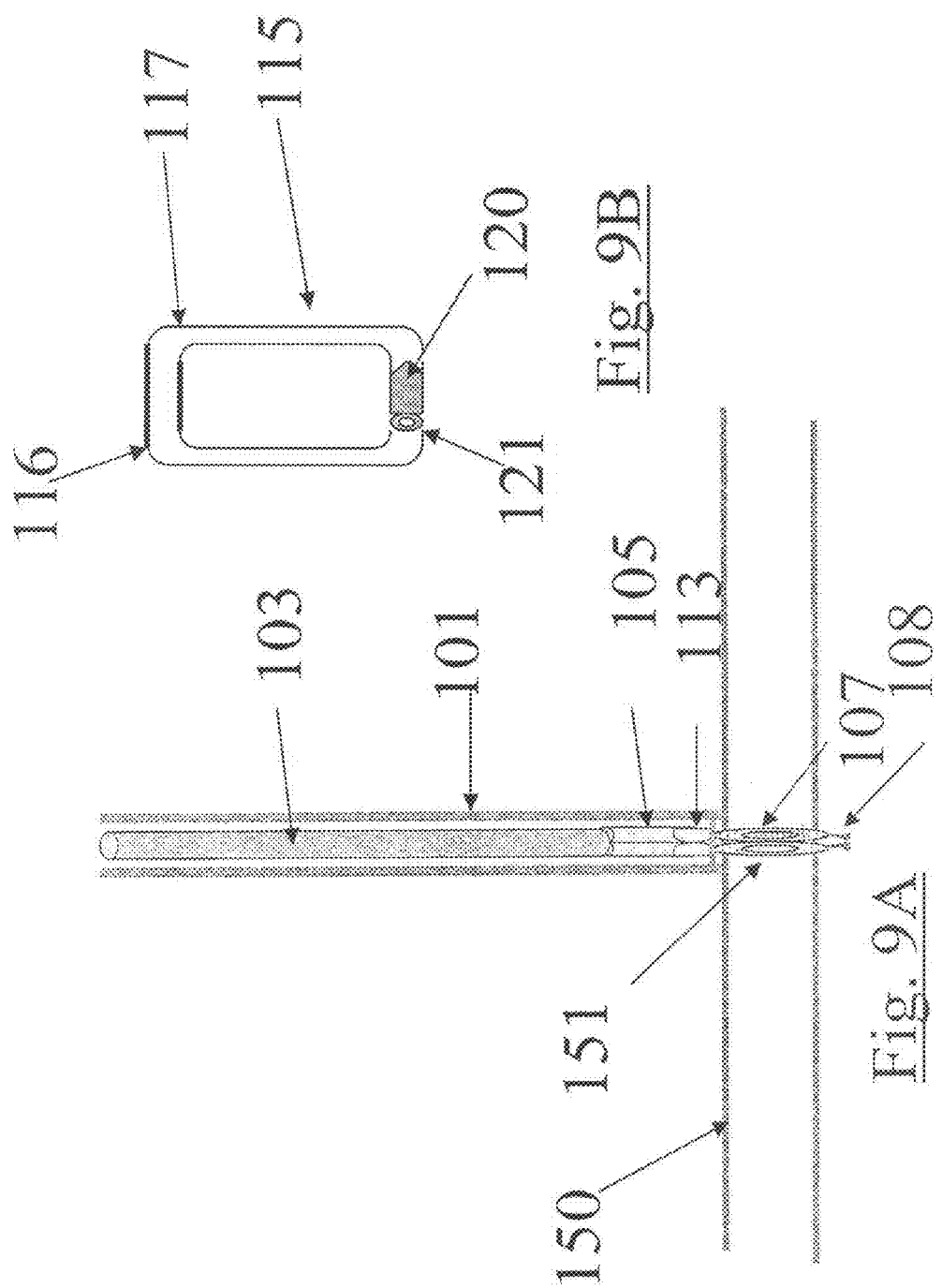

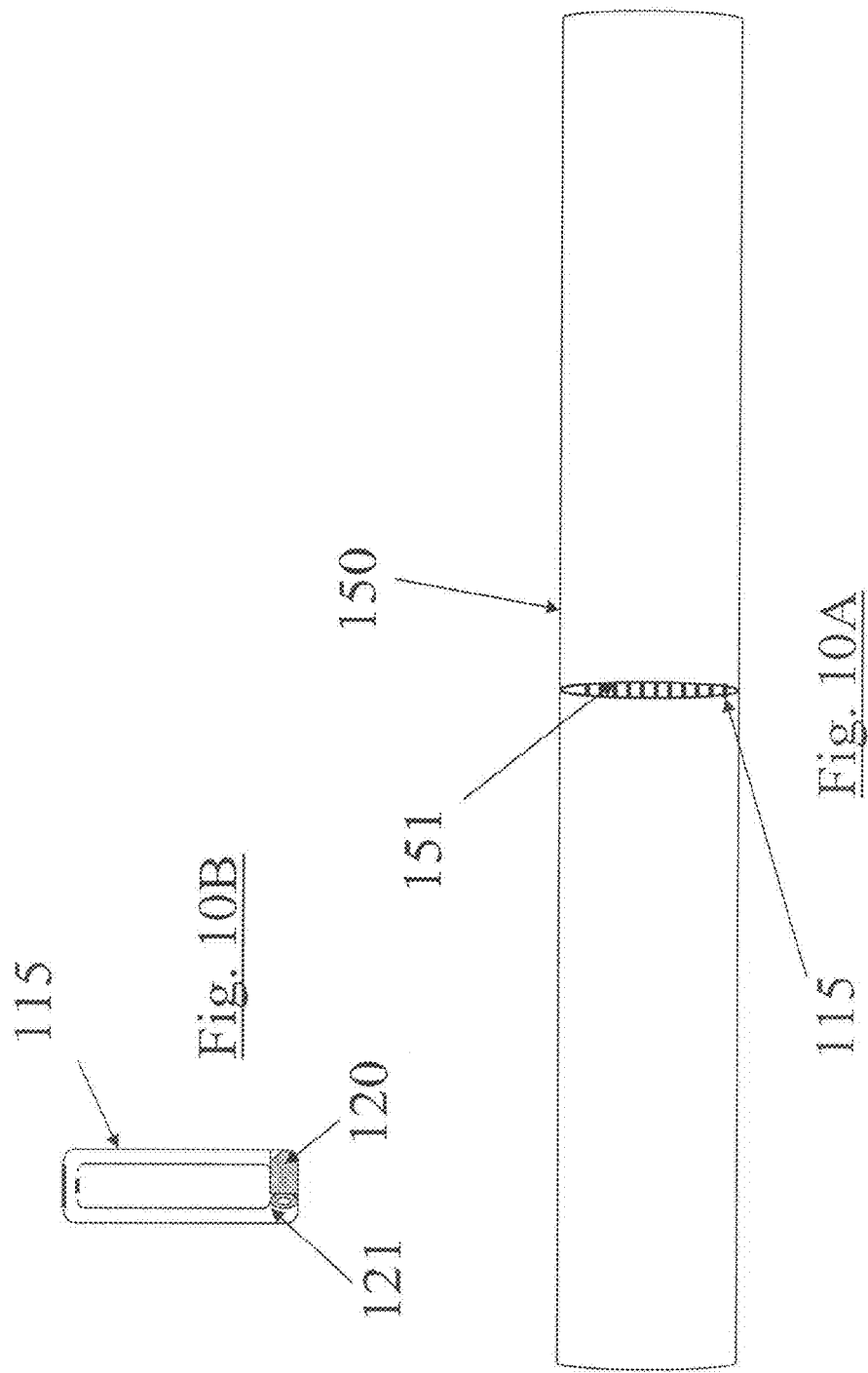

SUTURING DEVICE FOR ANASTOMISIS OF LUMENS

RELATED APPLICATION

This application claims priority to and incorporates by reference provisional application Ser. No. 61/043,320 entitled "Suturing Device for Anastomisis of Lumens" filed Apr. 8, 2008.

BACKGROUND

1. Field of the Invention

This invention relates generally to the field of surgical devices. More specifically, the invention relates to an apparatus and method of suturing or anastomizing of body lumens.

2. Background of the Invention

During minimally invasive surgical procedures, suturing of body tissue can be time consuming for the surgeon. In such endoscopic procedures, where surgery is performed in a body cavity and access to the site is through trocar cannulas, suturing is especially difficult. The surgeon cannot grasp the needle as in open surgery, but must rely on grasping instruments to grasp and maneuver the needle in the remote surgical site. These instruments entail grasping the surgical needle between the instrument jaws and manipulating the needle through the body tissue. Oftentimes, a second grasping instrument is required to enable passing the needle between the two instruments in the same manner the surgeon passes the needle during open procedures. Not only is maneuverability difficult, but the needle could slip from the jaws into the body cavity.

In addition, tying of suture knots is done with two legs of the suture thread protruding from a proximal end of a cannula or tube. Each throw of the suture knot (usually the knot requires four or five throws) is placed on the thread outside the cannula (outside the body of the patient) and the knot is pushed to its destination through the cannula with a tool commonly called a "knot pusher." Ultimately, the suture knot is tightened on or near the sutured organ, vessel or tissue at the surgical site. Plainly, conventional suturing is one of the more difficult, tedious and repetitive procedures in surgery.

Consequently, there is a need for a device and methods of quick anastomosis of tissues without use of traditional needles and thread.

BRIEF SUMMARY

Novel devices and methods for suturing together portions of a body lumen are disclosed herein. Embodiments of the device utilize inflatable members to capture the resected lumen portions and draw them together. Furthermore, embodiments of the device use suture rings and threadless suture clips to suture or connect the portions together to form a water tight seal. Further advantages and features of the invention will be described in more detail below.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which:

FIG. 5 illustrates the expansion of inflatable members in each vessel section;

FIG. 6 illustrates pulling the sections of the vessel together by retraction of the inner hollow body into outer hollow body;

FIG. 7A illustrates the sections of the vessels being drawn together with suture rings in place;

FIG. 7B illustrates a close-up of a suture clip (in its open position) that may be used in embodiments of the device;

FIG. 8A illustrates the sections of the vessels completely drawn together with the suture clips in closed position;

FIG. 8B illustrates a close-up of a surgical clip (with a narrowed opening) that may be used in embodiments of the device;

FIG. 9A illustrates collapse of inflatable members and retraction of the inner hollow body into the outer hollow body;

FIG. 9B illustrates the closed suture clip;

FIG. 10A illustrates the completely sutured or anastomized vessel; and

FIG. 10B illustrates the completely closed suture clip.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited

DETAILED DESCRIPTION OF THE PREFERRED EMBODIMENTS

Figure 1:
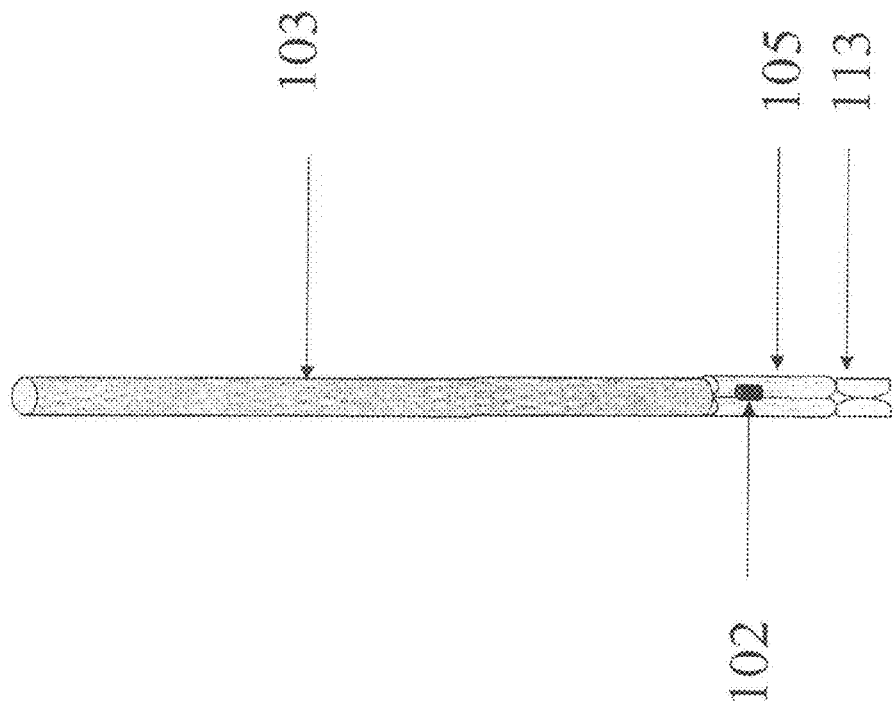
FIG. 1 illustrates the inner hollow body of an embodiment of a suturing device.
Figure 2:
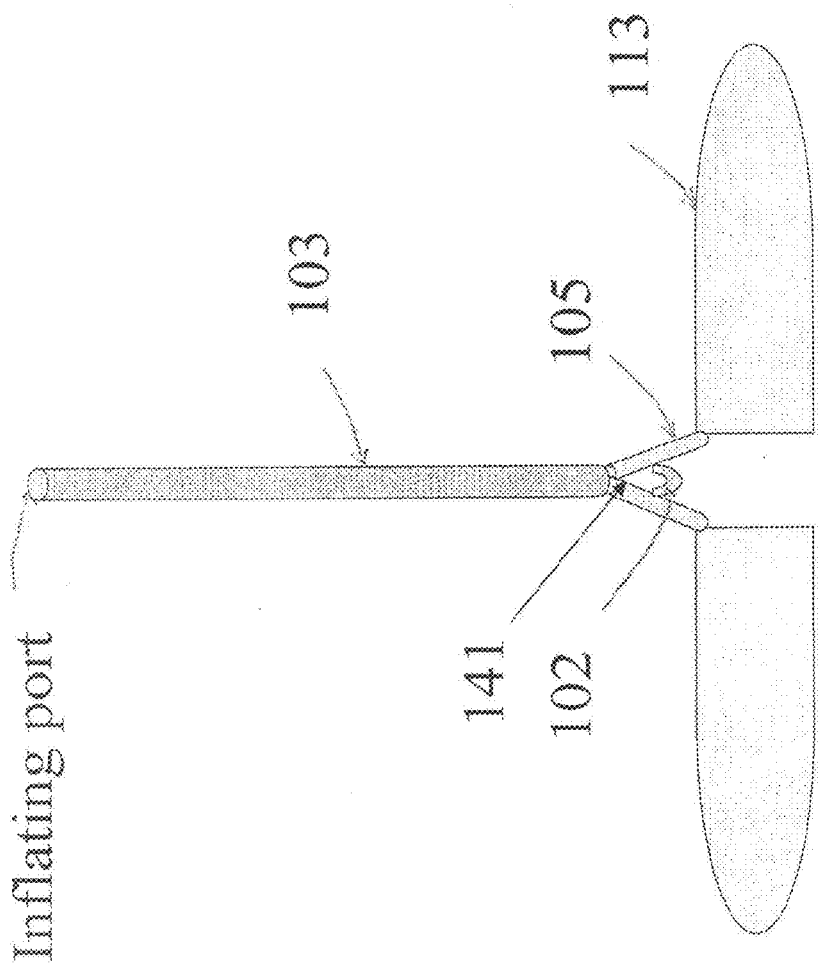
FIG. 2 illustrates the inner hollow body of the suturing device with the hollow arms in an open position and inflatable members in an expanded position.
Figure 3:
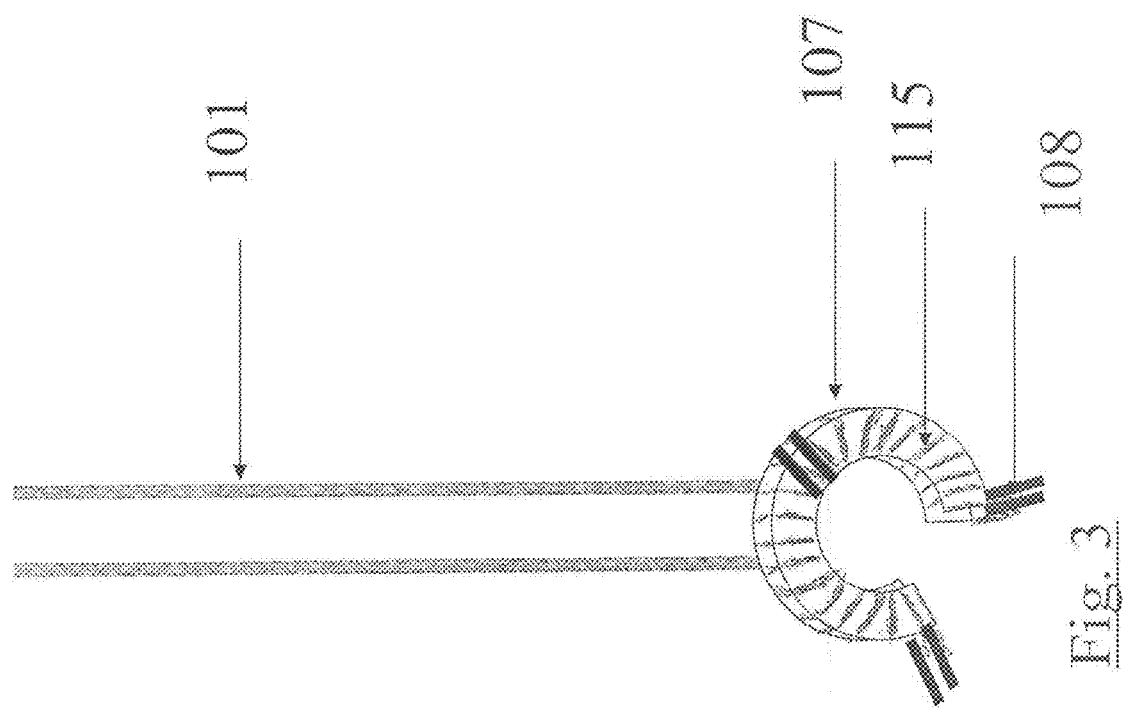
FIG. 3 illustrates the outer hollow body of the suturing device with a pair of suture rings coupled to the distal end of outer hollow body.
Figure 4:
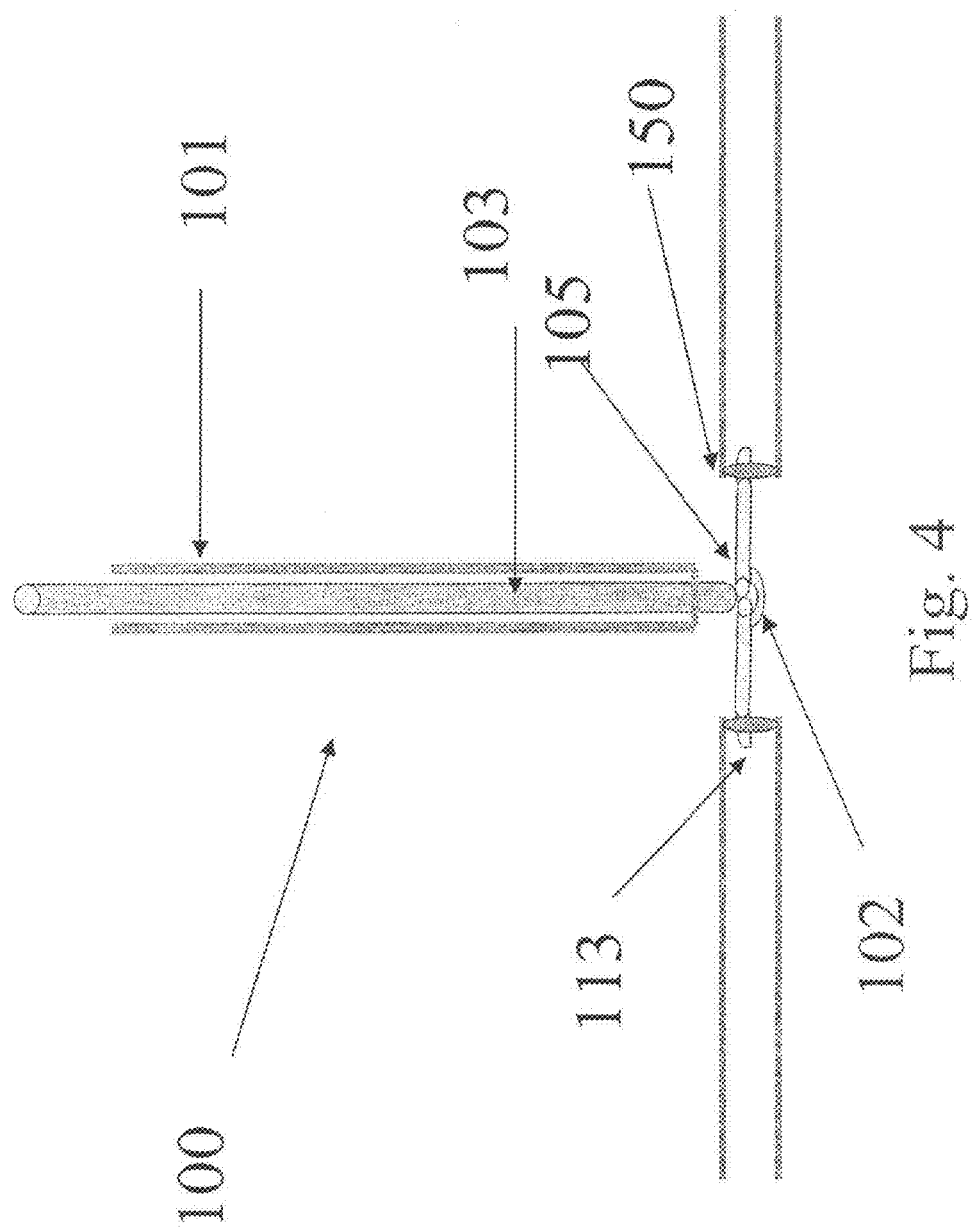
FIG. 4 illustrates the insertion of inflatable members into each section of vessel to be connected.

FIGS. 1-3 illustrate an embodiment of a suturing device having an outer hollow body 101 and an inner hollow body 103 with at least two hollow arms 105. In addition, outer hollow body 101 is coupled to a pair of detachable suture rings 107. In preferred embodiments, outer and inner hollow body 101, 103 are tubular in geometry. However, inner and outer hollow body 101, 103 may comprise any suitable geometry.

Inner hollow body 103 typically is slidably disposed within the lumen of outer hollow body 101. Thus, inner hollow body 103 may have a diameter that is smaller than the diameter of the outer hollow body 101. In some embodiments, inner and outer hollow body 101, 103 may comprise off the shelf catheters already known to those of skill in the art.

In an embodiment, inner hollow body 103 comprises at least two hollow arms 105 movably disposed at the distal end of inner hollow body 103. Moreover, hollow arms 105 each have a closed and open position. In the open position, hollow arms 105 are spread apart such that they are at an angle to inner hollow body. In a particular embodiment, hollow arms 105 are perpendicular to inner hollow body 103 in the open position.

The hollow arms 105 are preferably coupled to inner hollow body 103 by a joint 141. This joint 141 provides lateral movement to hollow arms 105, allowing them to spread apart. For example, joint 141 may comprise a spring joint 102 which snaps hollows arms 105 into each position, i.e., open or closed position.

Furthermore, each arm 105 comprises an inflatable member 113 or balloon coupled to its distal end. In at least one embodiment, each inflatable member 113 is movably attached to its respective arm. In other words, inflatable member 113 has free range of motion around hollow arm 105 to allow the surgeon flexibility in maneuvering vessels or tissues during suturing.

Inflatable member 113 for each arm 105 has an expanded and collapsed position. In the collapsed position, each collapsed member 113 has a diameter or cross-sectional area substantially the same as or less than that of each hollow arm 105. In the expanded or inflated position, the inflatable member 113 preferably has a cross-section substantially similar to the body lumen it is intended to be used for i.e. blood vessel, aorta, esophagus, etc. In general, inflatable member 113 is circular in cross-section. However, inflatable member may comprise any suitable shape as defined by the surgeon's needs.

Inflatable member 113 generally comprises a flexible, biocompatible material. Examples of such materials include without limitation, polymers, latex, silicone rubber, polyester, polyurethane, copolymers, polyethylene, polystyrene, or combinations thereof. The outer surface of each inflatable member 113 may be textured so as to easily grip or engage the inner surface of a vessel or lumen 150.

Referencing FIG. 3, in an embodiment, outer hollow body 101 is detachably coupled to a pair of suture rings 107. Suture rings 107 are coupled such that they are freely rotatable and maneuverable allowing a surgeon full freedom to manipulate the suture rings into the optimal position. The pair of suture rings are in parallel. In particular embodiments, suture rings 107 are hinged suture rings. That is, suture rings 107 also have an open and closed position via a hinge. The purpose of the hinged structure is so that the surgeon may clamp each suture ring round each section of the vessel. In other embodiments, suture rings 107 may comprise an opening mechanism such as a clasp. Generally, suture rings 107 may be of any diameter suitable for the vessel or body lumen to be anastomozed. Furthermore, suture rings 107 are preferably planar such that suture clips 107 may be attached to a flat surface. However, suture rings 107 may be of any suitable geometry.

Suture rings 107 may further comprise one or more handles or protrusions 108. These handles 108 may be textured to allow for improved grip by surgical tools. The handles 108 allow the surgeon to move suture rings into place and also to draw them together. In addition, handles 108 are made from a rigid material such as plastic or metal.

Suture rings 107 are coupled together by a plurality of surgical suture clips 115. In one embodiment, suture clips 115 are attached to suture rings 107 via a weak weld joint. Alternatively, suture clips 115 may be attached by a clipping mechanism, a snap-fit mechanism or other means of detachably attaching elements. Preferably, suture clips 115 are detachably attached to suture rings 107 so that surgeon can remove suture rings 107 from surgical suture clips 115, leaving only the suture clips 115 behind.

An example of a suture clip 115 that may be used with embodiments of the device is shown in FIGS. 7-10. Suture clips 115 generally comprise a first and second portion 116, 117 which are slidably disposed with respect to each other. In other words, first and second portion 116, 117 are capable of sliding together from an open to closed position. In the closed position, the portions 116, 117 of the suture clips 115 are locked into the closed position and cannot be re-opened. This aspect of the suture clip 115 ensures that the connection between tissue and clip will remain closed and the vessel remains sealed, once anastomized.

As shown in FIG. 9B, first portion 116 has a male connector 120 while second portion 117 has a female end 121. Male end 120 preferably is sharpened to a tip so as to be capable of penetrating or piercing tissue. Female end 121 is adapted to receive male end and prevent the suture clip 115 from opening once the male end is inserted. Tissue from each section of the vessel is caught between the male end and the female end. As each portion of suture clip 115 slides into closed position the male end 120 may pierce through the tissue into female end 121 and thus, suture the tissue together to form a water tight seal. In embodiments, suture rings 115 may be made of any rigid, biocompatible material such as plastics or metals. In a further embodiment, suture clips 115 may be made of a biodegradable polymer such as without limitation, poly(propylene fumarate), polylactic acid, polyglycolic acid, polycaprolactone, or combinations thereof.

In an embodiment of a method for connecting tissue, an embodiment of the above described device is provided. As mentioned above, it is envisioned that the disclosed methods and devices will be applicable to any body lumen such as arteries, veins, esophagus, intestine, urinary tract, and the like. However, for convenience, embodiments of a method for anastomosis or suturing will be described with respect to a blood vessel. The surgeon inserts the device into a patient to the desired suturing site. In general, inner hollow body 103 is fully retracted within outer hollow body 101 during insertion. Referencing FIG. 2, inner hollow body 103 may then be pushed outward such that hollow arms 105 move into their open position. In one embodiment, hollow arms 105 spring or pop into position because of a spring 102 force from the joint 141. Alternatively, hollow arms 105 may be moved manually using a surgical tool to the appropriate position.

Once hollow arms 105 are in position inflatable member 113 may be inserted into each section of the vessel to be connected. Inflatable members 113 are typically in their collapsed state when inserted. This may be accomplished by manipulation using surgical tools or other means known to those of skill in the art.

Inflatable members 113 are then expanded into an expanded position such that the outer surface of inflatable members engages the inner surface of the vessel. In some embodiments, inflatable members 113 may be expanded to an expanded position in which inflatable members 113 have a slightly greater diameter than the vessels. By doing so, this ensures that inflatable members 113 have properly engaged each vessel. Inflatable members 113 may be expanded by a fluid or a gas that has been forced through inner hollow body 103 and hollow arms 105.

When inflatable member 113 securely engages each section of the vessel, inner hollow body 103 may be withdrawn into outer hollow body 101. As inner hollow body 103 is retracted hollow arms 105 are forced together, which in turn also causes the sections of the blood vessel, 150 in FIG. 9A, to be drawn together as shown in FIGS. 6-7. Preferably, the edges of each vessel section are aligned with each other. At this point, suture rings 107, which are in their open position, may be positioned or clamped around each end section of the vessel. In at least one embodiment, suture rings 115 have a diameter in the closed position that is slightly smaller than the diameter of the vessel. In other words, when closed, suture rings 107 will slightly impinge or indent the outer surface of each vessel. Furthermore, suture rings 107 are clamped from 1 mm to about 5 mm from the end of each vessel section, leaving a small amount of tissue that suture clips 115 can pinch or suture together.

Once suture rings 107 are secured around each section of the vessel, suture rings 107 are drawn together by handles or protrusions projecting from suture rings. In an embodiment, the surgeon uses surgical tools such as tweezers or calipers to gently draw each suture ring 107 toward each other such that the first portion and second portion of suture clips 115 slide toward each other. The first portion comprises a male end 120 and second portion comprises a female end 121. The male and female ends may be drawn together such that the male end and female end engage each section of the vessel. The vessel ends are closed together as the suture clip is closed. Inflatable members 113 may then be contracted into their collapsed position and withdrawn into outer hollow body 101. When male end engages and connects with female end, the first and second portion are locked together. The surgeon may then detach suture clips 115 from the suture rings 107, and open suture rings 107 into their open positions. With suture rings 107 removed, the device 100 may be retracted from the surgical site, thus leaving the sections of the vessel completely anastomized without the need for needle and thread. FIG. 10A illustrates the fully sutured lumen 150 utilizing the technique and equipment disclosed herein, including a plurality of suture clips 115. The suture line 151 comprised of the plurality of closed suture clips holding the two lumen ends together, is also illustrated. Also illustrated is FIG. 10B showing a fully compressed or closed suture clip 115 comprising a closely joined male 120 and female 121 end forming a water tight seal. Not shown are the two ends of the lumen pierced by the suture clip.

While embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A method of connecting a first and a second portion of a body lumen comprising:
   a) providing a surgical device comprising a pair of parallel suture rings, wherein the pair of suture rings are coupled to each other by a plurality of suture clips, and at least two hollow arms, wherein each hollow arm is coupled to an inflatable member;
   b) capturing the first and second portion of the body lumen with the inflatable members;
   c) drawing the first and second portion of the body lumen together by pulling the hollow arms together;
   d) clamping the ends of the first and second portion of the body lumen with the pair of suture rings; and
   e) locking the plurality of suture clips together to connect the first and second portion of the body lumen.

2. The method of claim 1, further comprising detaching the plurality of suture clips from the suture rings.

3. The method of claim 1, wherein b) comprises expanding the inflatable members to capture the first and the second portion of the body lumen.

4. The method of claim 1, wherein the surgical device further comprises an outer hollow body coupled to the suture rings and a inner hollow body coupled to the hollow arms, wherein the inner hollow body is disposed within the outer hollow body.

5. The method of claim 4, further comprising pushing inner hollow body out of outer hollow body such that the hollow arms spring outwardly.

6. The method of claim 4, wherein c) comprises retracting inner hollow body into outer hollow body to draw the hollow arms together.

7. The method of claim 1, wherein the plurality of suture clips comprises a sharp male end and a female end adapted to receive the male end.

8. The method of claim 7, wherein e) comprises piercing the ends of the first and second portion between the male end and the female end to connect the first and second portion of the body lumen.

* * * * *